(12) United States Patent
Narita

(10) Patent No.: US 12,340,625 B2
(45) Date of Patent: Jun. 24, 2025

(54) IN-VEHICLE APPARATUS, DRINKING DETERMINATION METHOD, AND STORAGE MEDIUM

(71) Applicant: NEC Corporation, Tokyo (JP)

(72) Inventor: Kyohei Narita, Tokyo (JP)

(73) Assignee: NEC CORPORATION, Tokyo (JP)

( * ) Notice: Subject to any disclaimer, the term of this patent is extended or adjusted under 35 U.S.C. 154(b) by 347 days.

(21) Appl. No.: 17/802,618

(22) PCT Filed: Mar. 11, 2020

(86) PCT No.: PCT/JP2020/010602
§ 371 (c)(1),
(2) Date: Aug. 26, 2022

(87) PCT Pub. No.: WO2021/181574
PCT Pub. Date: Sep. 16, 2021

(65) Prior Publication Data
US 2023/0142517 A1 May 11, 2023

(51) Int. Cl.
G06K 9/00 (2022.01)
B60K 28/06 (2006.01)
B60K 28/12 (2006.01)
G06V 20/58 (2022.01)
G06V 40/10 (2022.01)
G06V 40/20 (2022.01)

(52) U.S. Cl.
CPC ............ *G06V 40/25* (2022.01); *B60K 28/063* (2013.01); *B60K 28/12* (2013.01); *G06V 20/58* (2022.01); *G06V 40/10* (2022.01)

(58) Field of Classification Search
CPC ........ G06V 40/25; G06V 20/58; G06V 40/10; G06V 20/597; B60K 28/063; B60K 28/12; B60W 2420/403; B60W 2540/24; A61B 5/11
See application file for complete search history.

(56) References Cited

U.S. PATENT DOCUMENTS 9,767,694 B1 * 9/2017 Wells .................. A61B 5/0022
2014/0316663 A1 * 10/2014 Hyde ....................... G01F 23/80
701/1
2017/0055881 A1 3/2017 Kang et al.

FOREIGN PATENT DOCUMENTS

| CN | 107618369 A | 1/2018 |
| JP | 2005-335521 A | 12/2005 |
| JP | 2007-295948 A | 11/2007 |
| JP | 2008-265507 A | 11/2008 |
| JP | 2009-219579 A | 10/2009 |
| JP | 2011-057156 A | 3/2011 |
| JP | 2019-190185 A | 10/2019 |

OTHER PUBLICATIONS

JP Office Action for JP Application No. 2022-507090, mailed on Feb. 20, 2024 with English Translation.
International Search Report for PCT Application No., PCT/JP2020/010602, mailed on Jun. 9, 2020.

* cited by examiner

*Primary Examiner* — Dhaval V Patel

(57) ABSTRACT

An in-vehicle apparatus according to the present disclosure includes: estimated walking path acquisition means for acquiring an estimated walking path, which is a path in which it is estimated that a driver will walk; and drinking determination means for determining whether or not the driver is drunk based on a walking pattern of the driver in the estimated walking path.

11 Claims, 7 Drawing Sheets

IN-VEHICLE APPARATUS, DRINKING DETERMINATION METHOD, AND STORAGE MEDIUM

This application is a National Stage Entry of PCT/JP2020/010602 filed on Mar. 11, 2020, the contents of all of which are incorporated herein by reference, in their entirety.

TECHNICAL FIELD

The present disclosure relates to an in-vehicle apparatus, a drinking determination method, and a storage medium.

BACKGROUND ART

An apparatus that captures an image of a driver, compares this captured image with an image of this driver in a normal time (when he/she is not drunk), and thus determines whether or not this driver is drunk is disclosed in, for example, Patent Literature 1.

CITATION LIST

Patent Literature

[Patent Literature 1] Japanese Unexamined Patent Application Publication No. 2007-295946

SUMMARY OF INVENTION

Technical Problem

However, the apparatus disclosed in Patent Literature 1 only determines whether or not a driver is drunk inside a vehicle. That is, it does not determine whether or not the driver is drunk outside the vehicle.

In view of the aforementioned problem, an object of the present disclosure is to provide an in-vehicle apparatus, a drinking determination method, and a storage medium capable of determining whether or not a driver is drunk outside a vehicle.

Solution to Problem

An in-vehicle apparatus according to a first aspect of the present disclosure includes: estimated walking path acquisition means for acquiring an estimated walking path, which is a path in which it is estimated that a driver will walk; and drinking determination means for determining whether or not the driver is drunk based on a walking pattern of the driver with respect to the estimated walking path.

A drinking determination method according to a second aspect of the present disclosure includes: an estimated walking path acquisition step for acquiring an estimated walking path, which is a path in which it is estimated that a driver will walk; and a drinking determination step for determining whether or not the driver is drunk based on a walking pattern of the driver with respect to the estimated walking path.

A storage medium according to a third aspect of the present disclosure is a computer readable storage medium storing a program for causing an electronic device including at least one processor to execute: estimated walking path acquisition processing for acquiring an estimated walking path, which is a path in which it is estimated that a driver will walk; and drinking determination processing for determining whether or not the driver is drunk based on a walking pattern of the driver with respect to the estimated walking path.

Advantageous Effects of Invention

According to the present invention, it is possible to provide an in-vehicle apparatus, a drinking determination method, and a storage medium capable of determining whether or not a driver is drunk outside a vehicle.

EXAMPLE EMBODIMENT

First Example Embodiment

Hereinafter, with reference to the accompanying drawings, an in-vehicle apparatus 1 (a drinking determination apparatus) according to a first example embodiment of the present disclosure will be described. Throughout the drawings, the corresponding components are denoted by the same reference symbols and overlapping descriptions are omitted.

First, with reference to FIG. 1, a configuration of the in-vehicle apparatus 1 will be described.

Figure 1:
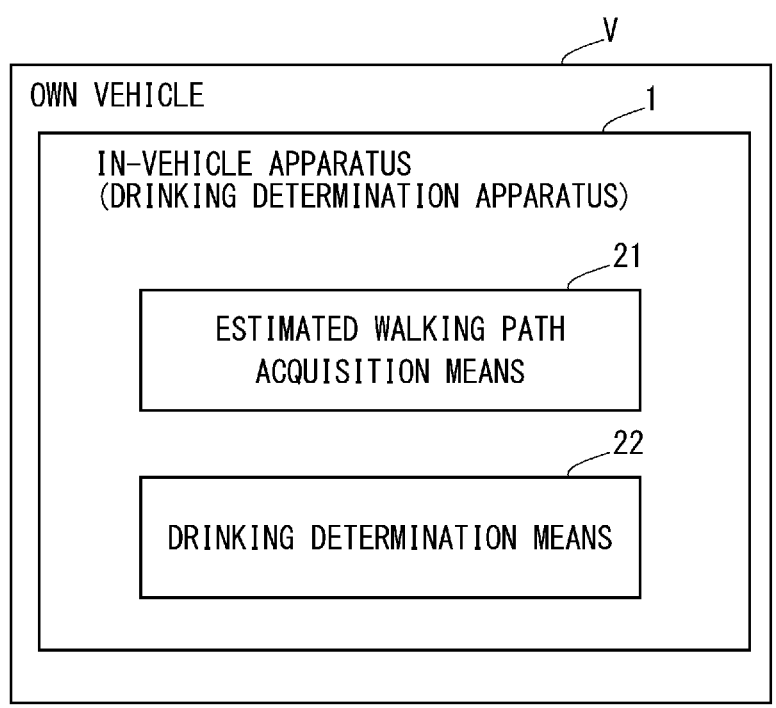
FIG. 1 is a schematic configuration diagram of an in-vehicle apparatus 1.

FIG. 1 is a schematic configuration diagram of the in-vehicle apparatus 1. Hereinafter, it is assumed that the in-vehicle apparatus 1 is mounted on an own vehicle V.

As shown in FIG. 1, the in-vehicle apparatus 1 includes estimated walking path acquisition means 21 for acquiring an estimated walking path, which is a path in which it is estimated that a driver of the own vehicle V will walk, and drinking determination means 22 for determining whether or not the driver of the own vehicle V is drunk based on a walking pattern of the driver of the own vehicle in the estimated walking path.

Next, one example of an operation of the in-vehicle apparatus 1 having the aforementioned configuration will be described.

Figure 2:
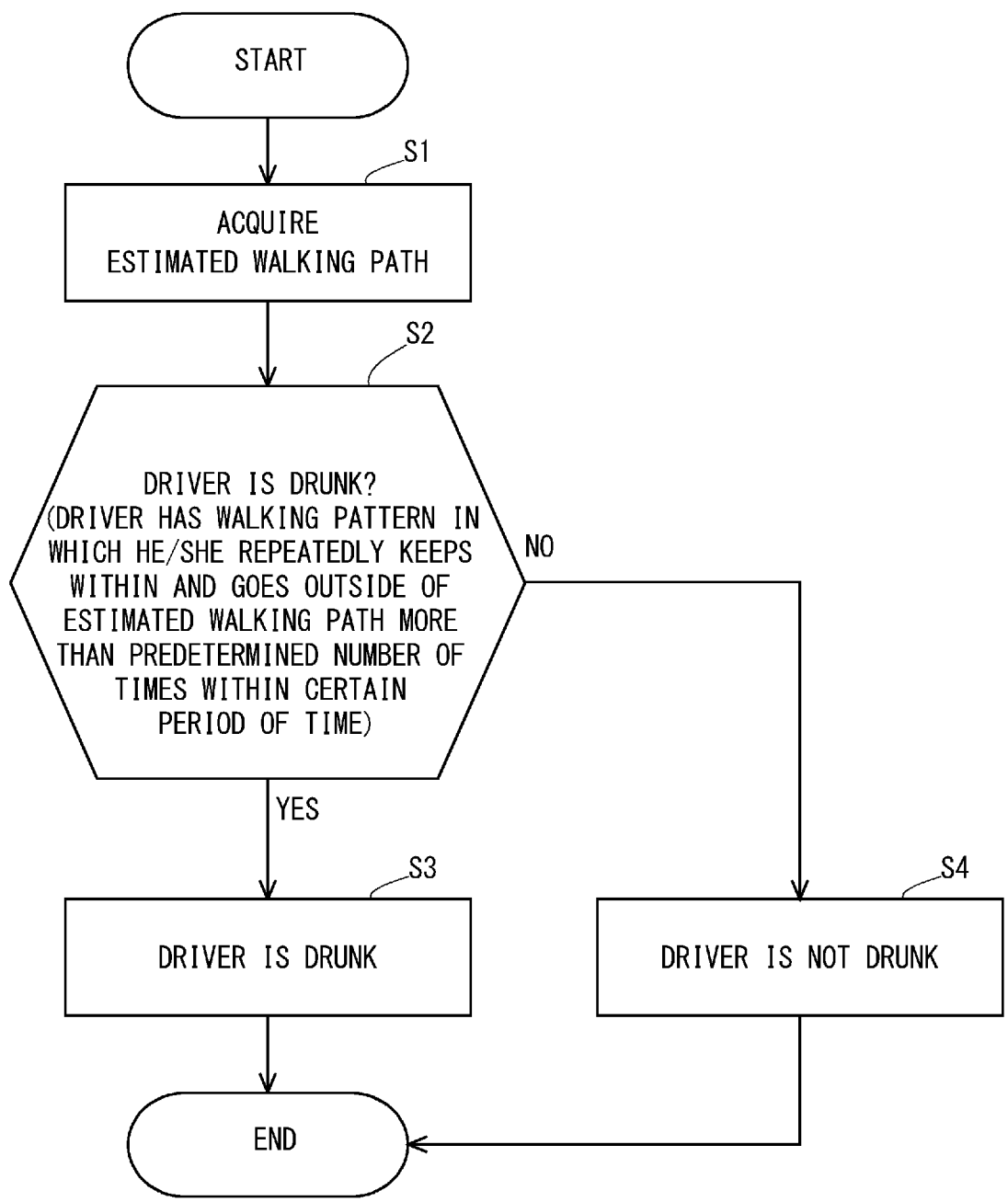
FIG. 2 is a flowchart showing one example of an operation of the in-vehicle apparatus 1.

FIG. 2 is a flowchart of one example of the operation of the in-vehicle apparatus 1.

First, the in-vehicle apparatus 1 (the estimated walking path acquisition means 21) acquires the estimated walking path, which is a path in which it is estimated that the driver of the own vehicle V will walk (Step S1).

Next, the in-vehicle apparatus 1 (the drinking determination means 22) determines whether or not the driver of the own vehicle V is drunk based on the walking pattern of the driver of the own vehicle in the estimated walking path acquired in Step S1 (Step S2). The drinking determination means 22 determines, for example, whether or not the driver of the own vehicle V has a walking pattern in which he/she repeatedly keeps within and then goes outside of the width of the estimated walking path more than a predetermined number of times within a certain period of time. If the driver has repeated the above walking pattern more than the predetermined number of times (Step S2: YES), it is determined that the driver of the own vehicle V is drunk (Step S3). On the other hand, if the driver has not repeated the above walking pattern more than the predetermined number of times (Step S2: NO), it is determined that the driver of the own vehicle V is not drunk (Step S3).

According to the first example embodiment, it is possible to determine whether or not the driver of the own vehicle V is drunk outside the vehicle based on the walking pattern of the driver of the own vehicle V.

Second Example Embodiment

Hereinafter, as a second example embodiment of the present invention, the in-vehicle apparatus 1 (the drinking determination apparatus) according to the first example embodiment will be described in further detail.

Figure 3:
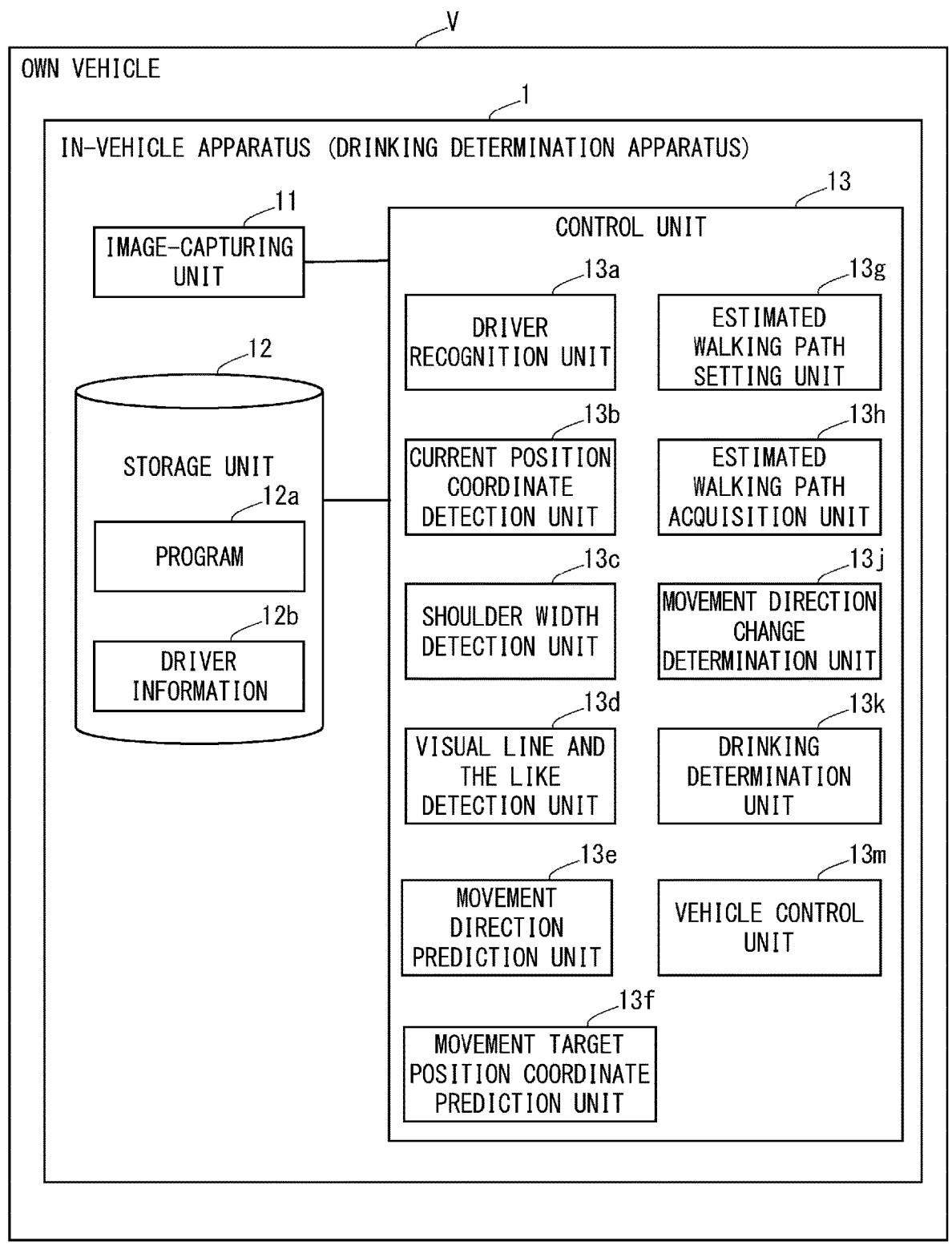
FIG. 3 is a detailed configuration diagram of the in-vehicle apparatus 1.
Figure 4:
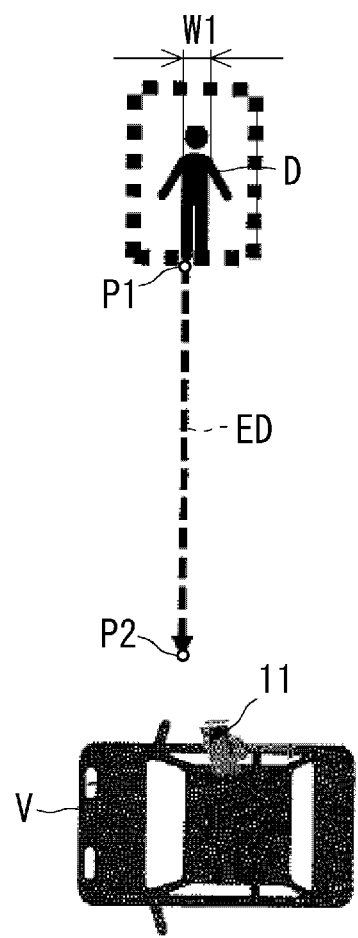
FIG. 4 is a schematic diagram indicating a relation and the like between an own vehicle V and a driver D of the own vehicle V.
Figure 5:
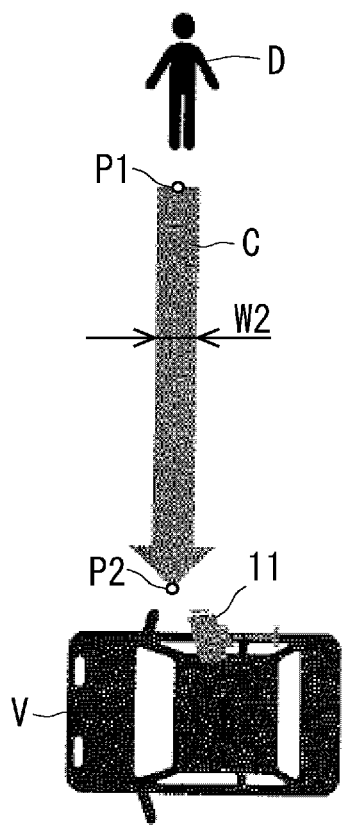
FIG. 5 is a schematic diagram indicating a relation and the like between the own vehicle V and the driver D of the own vehicle V.
Figure 6:
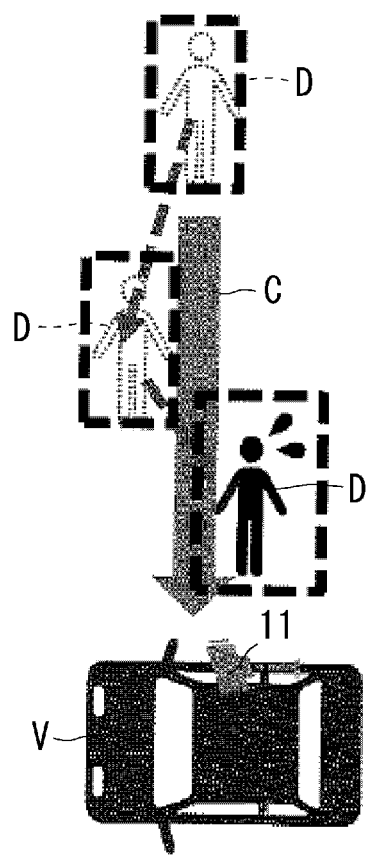
FIG. 6 is a schematic diagram indicating a relation and the like between the own vehicle V and the driver D of the own vehicle V.

FIG. 3 is a detailed configuration diagram of the in-vehicle apparatus 1. FIGS. 4-6 are schematic diagrams each showing a relation and the like between the own vehicle V and the driver D of the own vehicle V. In the following description, it is assumed that the in-vehicle apparatus 1 is mounted on the own vehicle V. In the second example embodiment, an estimated walking path acquisition unit 13h is used as the estimated walking path acquisition means 21 and a drinking determination unit 13k is used as the drinking determination means 22.

As shown in FIG. 3, the in-vehicle apparatus 1 mainly includes, as a hardware configuration, an image-capturing unit 11, a storage unit 12, and a control unit 13.

The image-capturing unit 11 is an image-capturing apparatus (camera) including an image-capturing element such as a CCD sensor or a CMOS sensor. The image-capturing unit 11 captures an image including a driver D (see FIG. 4) who is walking toward the own vehicle V. The image-capturing unit 11 is attached, for example, to a side part of the own vehicle V so that the image-capturing unit 11 is able to capture an image of the exterior of the side of the own vehicle V, as shown in FIG. 4. The image-capturing unit 11 may instead be attached to the front part of the own vehicle V so that it can capture an image of the exterior of the front of the own vehicle V, attached to the rear part of the own vehicle V so that it can capture an image of the exterior of the rear of the own vehicle V, or attached to another part of the own vehicle V.

The storage unit 12 is, for example, a non-volatile storage unit such as a hard disk drive or a ROM. The storage unit 12 stores a program 12a, driver information 12b and the like.

The program 12a is a program executed by the control unit 13 (processor). The driver information 12b is, for example, data indicating features (feature points) extracted from a face image of the driver D of the own vehicle V.

The control unit 13 is, for example, an Electronic Control Unit (ECU). The control unit 13 includes a processor, although it is not shown in the drawing. The processor is, for example, a CPU. The number of processors may either be one or a plural number. The processor executes the program 12a loaded into a RAM (not shown) from the storage unit 12, whereby the processor functions as a driver recognition unit 13a, a current position coordinate detection unit 13b, a shoulder width detection unit 13c, a visual line and the like detection unit 13d, a movement direction prediction unit 13e, a movement target position coordinate prediction unit 13f, an estimated walking path setting unit 13g, an estimated walking path acquisition unit 13h, a movement direction change determination unit 13j, a drinking determination unit 13k, and a vehicle control unit 13m, as shown in FIG. 3. Some or all of them may instead be implemented by hardware.

The driver recognition unit 13a recognizes the driver D of the own vehicle V. The driver recognition unit 13a recognizes the driver D of the own vehicle V by extracting, for example, data representing features of the face of this person from the image (image including at least one person) captured by the image-capturing unit 11 and comparing this extracted data representing the features with the driver information 12b stored in the storage unit 12.

The current position coordinate detection unit 13b detects current position coordinates P1 (see FIG. 4) of the driver D of the own vehicle V. The current position coordinate detection unit 13b detects the current position coordinates P1 of the driver D of the own vehicle V by executing, for example, predetermined image processing on the image (the image including the driver D of the own vehicle V) captured by the image-capturing unit 11. Simultaneous Localization and Mapping (SLAM) may be, for example, used to detect the current position coordinates P1 of the driver D of the own vehicle V.

The shoulder width detection unit 13c detects a shoulder width W1 (see FIG. 4) of the driver D of the own vehicle V. The shoulder width detection unit 13c detects the shoulder width W1 of the driver D of the own vehicle V by executing, for example, predetermined image processing on the image (the image including the driver D of the own vehicle V) captured by the image-capturing unit 11.

The visual line and the like detection unit 13d detects at least one of the line-of-sight (line-of-sight direction) and the orientation of the body of the driver D of the own vehicle V. The visual line and the like detection unit 13d detects at least one of the line-of-sight direction and the orientation of the body of the driver D of the own vehicle V by executing, for example, known line-of-sight detection processing on the image (the image including the driver D of the own vehicle V) captured by the image-capturing unit 11.

The movement direction prediction unit 13e predicts the movement direction of the driver D of the own vehicle V (see the dotted arrow shown by the reference symbol ED in FIG. 4). Hereinafter, this moving direction will be referred to as a movement direction ED. The movement direction prediction unit 13e predicts, for example, at least one of the line-of-sight and the orientation of the body of the driver D of the own vehicle V detected by the visual line and the like detection unit 13d as the movement direction ED of the driver D of the own vehicle V.

The movement target position coordinate prediction unit 13f predicts movement target position coordinates P2 (see FIG. 4) of the driver D of the own vehicle V. The movement target position coordinate prediction unit 13f predicts, for example, a position that is apart from the current position coordinates P1 of the driver D of the own vehicle V by a predetermined distance (for example, several meters ahead) in the movement direction ED as the movement target position coordinates P2 of the driver D of the own vehicle V. This predetermined distance may be, for example, the one stored in the storage unit 12 in advance.

The estimated walking path setting unit 13g sets (defines) an estimated walking path C (see FIG. 5), which is a path (route) along which it is estimated that the driver D of the own vehicle V will walk. As shown in FIG. 5, the estimated walking path C is, for example, a straight line that connects the current position coordinates P1 of the driver D of the own vehicle V and the movement target position coordinates P2. The estimated walking path C has a width W2. This width W2 is, for example, the shoulder width W1 of the driver D of the own vehicle V detected by the shoulder width detection unit 13c.

The estimated walking path acquisition unit 13h acquires the estimated walking path C. For example, the estimated walking path acquisition unit 13h acquires the estimated walking path C set by the estimated walking path setting unit 13g. The estimated walking path C is specified by the current position coordinates P1, the movement target position coordinates P2, and the width W2. The estimated walking path acquisition unit 13h may instead acquire an estimated walking path C stored in the storage unit 12 in advance (for example, a case in which the own vehicle is parked in a parking space at a house and the walking path of the driver D of the own vehicle V is always the same). Further, the estimated walking path acquisition unit 13h may acquire the estimated walking path C from an external server by a wireless communication unit (not shown).

The movement direction change determination unit 13j determines whether or not the movement direction ED of the driver D of the own vehicle V has been changed. The movement direction change determination unit 13j determines, for example, whether or not at least one of the line-of-sight and the orientation of the body of the driver D of the own vehicle V has been changed by more than a threshold. This threshold may be, for example, the one stored in the storage unit 12 in advance. The movement direction change determination unit 13j determines, for example, whether or not the angle difference between the movement direction of the driver D of the own vehicle V detected based on the image captured by the image-capturing unit 11 at a certain timing and the movement direction of the driver D of the own vehicle V detected based on the image captured by the image-capturing unit 11 at the next timing exceeds a threshold. If the angle difference exceeds the threshold, it is determined that the movement direction of the driver D of the own vehicle V has been changed. On the other hand, if the angle difference does not exceed the threshold, it is determined that the movement direction of the driver D of the own vehicle V has not been changed.

The drinking determination unit 13k determines whether or not the driver D of the own vehicle V is drunk based on the walking pattern of the driver D of the own vehicle V in the estimated walking path C.

The drinking determination unit 13k determines, for example, whether or not the driver D of the own vehicle V (the current position coordinates of the driver D of the own vehicle V) has a walking pattern (see FIG. 6) in which he/she repeatedly keeps within and then goes outside of the width W2 of the estimated walking path C more than a predetermined number of times within a certain period of time (for example, several seconds). If the driver D has repeated the walking pattern more than the predetermined number of times, it is determined that the driver D of the own vehicle V is drunk. On the other hand, if the driver D has not repeated the above walking pattern more than the predetermined number of times, it is determined that the driver D of the own vehicle V is not drunk. The certain period of time and the predetermined number may be, for example, those stored in the storage unit 12 in advance.

If it has been determined by the drinking determination unit 13k that the driver D of the own vehicle V is drunk, for example, if it has been determined that the driver D of the own vehicle V has the walking pattern in which he/she repeatedly keeps within and then goes outside of the width W2 of the estimated walking path C within a certain period of time, the vehicle control unit 13m controls the vehicle that the driver D of the own vehicle V is planning to drive (i.e., the own vehicle V) so as not to allow the driver D of the own vehicle V to drive. For example, the vehicle control unit 13m controls the vehicle that the driver D of the own vehicle V is planning to drive in such a way that the engine of the vehicle cannot be started. Alternatively, the vehicle control unit 13m locks the door of the vehicle that the driver D is planning to drive so that he/she cannot open the door.

Next, one example of the operation of the in-vehicle apparatus 1 having the aforementioned configuration will be described.

Figure 7:
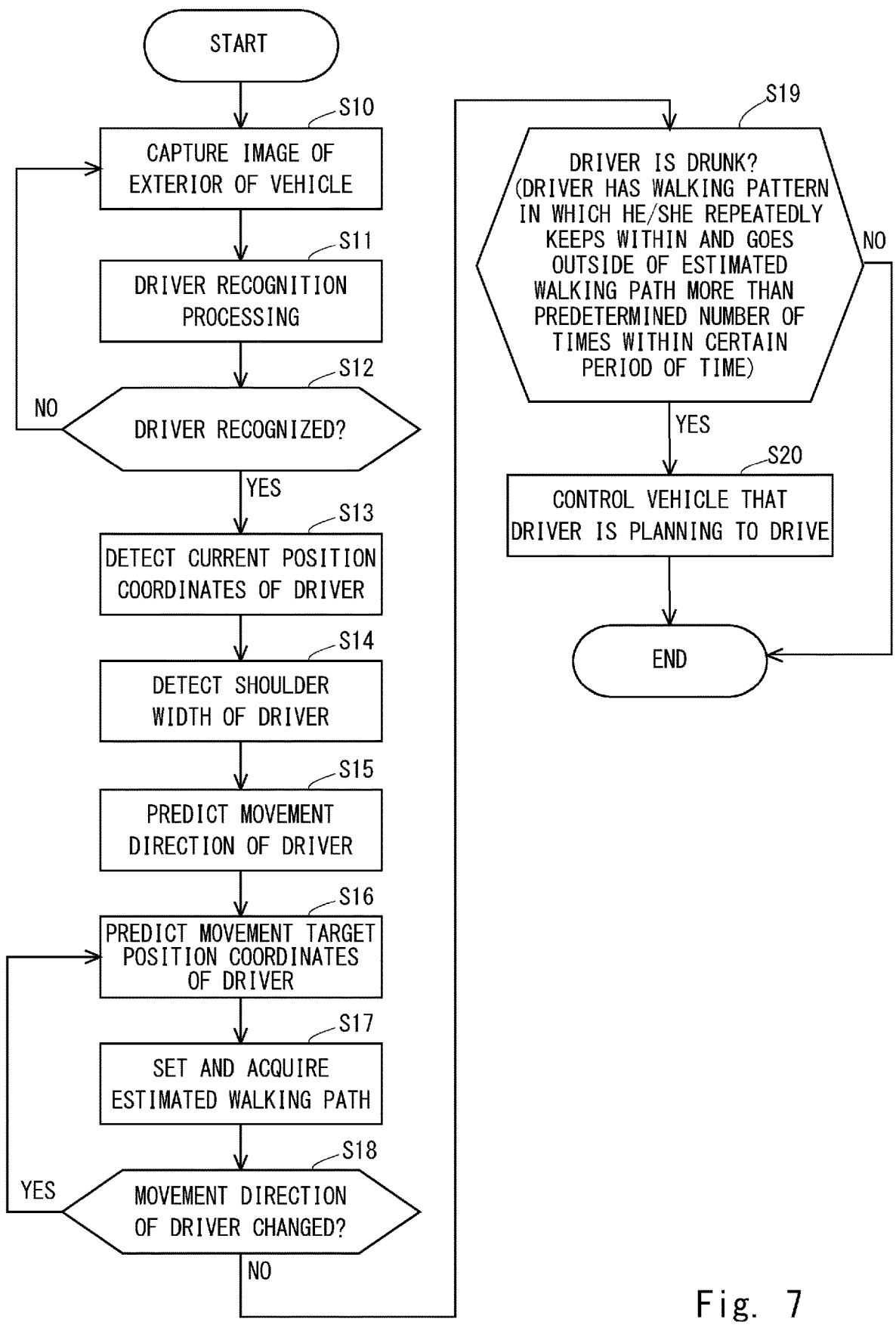
FIG. 7 is a flowchart of one example of an operation of the in-vehicle apparatus 1.

FIG. 7 is a flowchart of one example of an operation of the in-vehicle apparatus 1. The processing of FIG. 7 is achieved by the control unit 13 (processor) executing the program 12a read into a RAM (not shown) from the storage unit 12.

It is assumed, in the following description, that the image-capturing unit 11 captures an image of the exterior of the side of the own vehicle V at a predetermined frame rate.

First, the in-vehicle apparatus 1 (the image-capturing unit 11) captures the image of the exterior of the side of the own vehicle V (Step S10). It is assumed here that an image including a person has been taken.

Next, the in-vehicle apparatus 1 (the driver recognition unit 13a) executes driver recognition processing for recognizing the driver D of the own vehicle V (Step S11). For example, the driver recognition unit 13a recognizes the driver D of the own vehicle V by extracting, from the image including the person captured in Step S10, data representing features of the face of this person and comparing the extracted data representing the features with the driver information 12b stored in the storage unit 12.

If the result of Step S11 shows that the driver D of the own vehicle V has been successfully recognized (Step S12: YES), the in-vehicle apparatus 1 (the current position coordinate detection unit 13b) detects the current position coordinates P1 (see FIG. 4) of the driver D of the own vehicle V (Step S13).

Next, the in-vehicle apparatus 1 (the shoulder width detection unit 13c) detects the shoulder width W1 (see FIG. 4) of the driver D of the own vehicle V (Step S14).

Next, the in-vehicle apparatus 1 (the movement direction prediction unit 13e) predicts the movement direction ED (see FIG. 4) of the driver D of the own vehicle V. The movement direction prediction unit 13e predicts, for example, at least one of the line-of-sight and the orientation of the body of the driver D of the own vehicle V detected by the visual line and the like detection unit 13d as the movement direction ED of the driver D of the own vehicle V (Step S15).

Next, the in-vehicle apparatus 1 (the movement target position coordinate prediction unit 13f) predicts the movement target position coordinates P2 (see FIG. 4) of the driver D of the own vehicle V (Step S16). For example, the movement target position coordinate prediction unit 13f predicts a position located away from the current position coordinates P1 of the driver D of the own vehicle V detected in Step S13 by a predetermined distance (for example, several meters ahead) in the movement direction ED predicted in Step S15 as the movement target position coordinates P2 of the driver D of the own vehicle V.

Next, the in-vehicle apparatus 1 (the estimated walking path setting unit 13g) sets (defines) the estimated walking path C (see FIG. 5) (Step S17). The estimated walking path C is, for example, a straight line that connects the current position coordinates P1 of the driver D of the own vehicle V detected in Step S13 and the movement target position coordinates P2 predicted in Step S16. The width W2 of the estimated walking path C is the shoulder width W1 of the driver D of the own vehicle V detected in Step S14.

Next, the in-vehicle apparatus 1 (the estimated walking path acquisition unit 13h) acquires the estimated walking path C set in Step S17 (Step S17).

Next, the in-vehicle apparatus 1 (the movement direction change determination unit 13j) determines whether or not the movement direction ED of the driver D of the own vehicle V has been changed (Step S18). The movement direction change determination unit 13j determines, for example, whether or not at least one of the line-of-sight and the orientation of the body of the driver D of the own vehicle V has been changed by more than a threshold.

If the result of Step S18 shows that the movement direction ED of the driver D of the own vehicle V has been changed (Step S18: YES), the processing of Steps S16 and S17 is repeatedly executed.

On the other hand, if the result of Step S18 shows that the movement direction ED of the driver D of the own vehicle V has not been changed (Step S18: NO), the in-vehicle apparatus 1 (the drinking determination unit 13k) determines whether or not the driver D of the own vehicle V is drunk based on the walking pattern of the driver D of the own vehicle V in the estimated walking path C acquired in Step S17 (Step S19). The drinking determination unit 13k determines, for example, whether or not the driver D of the own vehicle V has the walking pattern (see FIG. 6) in which he/she repeatedly keeps within and then goes outside of the width W2 of the estimated walking path C more than a predetermined number of times in a certain period of time. If the walking pattern has been repeated more than the predetermined number of times (Step S19: YES), it is determined that the driver D of the own vehicle V is drunk. On the other hand, if the walking pattern has not been repeated more than the predetermined number of times (Step S19: NO), it is determined that the driver D of the own vehicle V is not drunk.

If the result of Step S19 shows that the driver D of the own vehicle V is drunk (Step S19: YES), that is, if it is determined that the driver D of the own vehicle V has the walking pattern in which he/she repeatedly keeps within and then goes outside of the width W2 of the estimated walking path C more than a predetermined number of times within a certain period of time, the in-vehicle apparatus 1 (the vehicle control unit 13m) controls the vehicle that the driver D of the own vehicle V is planning to drive (i.e., the own vehicle V) so as not to allow the driver D of the own vehicle V to drive (Step S20). The vehicle control unit 13m controls, for example, the vehicle that the driver D of the own vehicle V is planning to drive in such a way that the engine of the vehicle cannot be started. Alternatively, the vehicle control unit 13m locks the door of the own vehicle V that the driver D is planning to drive so that the driver D cannot open the door of the vehicle.

On the other hand, if the result of Step S19 shows that the driver D of the own vehicle V is not drunk (Step S19: NO), i.e., if it is determined that the driver D of the own vehicle V does not have the walking pattern in which he/she repeatedly keeps within and then goes outside of the width W2 of the estimated walking path C more than a predetermined number of times within a certain period of time, the in-vehicle apparatus 1 (the vehicle control unit 13m) ends the processing of FIG. 7 without controlling the vehicle that the driver D of the own vehicle V is planning to drive (i.e., the own vehicle V).

As described above, according to the second example embodiment, it is possible to determine whether or not the driver D of the own vehicle V is drunk outside the vehicle based on the walking pattern of the driver D of the own vehicle V.

Further, according to the second example embodiment, if it has been determined that the driver D of the own vehicle V is drunk (Step S19: YES), it is possible to control the vehicle that the driver D of the own vehicle V is planning to drive (i.e., the own vehicle V) so as not to allow the driver D of the own vehicle V to drive (Step S20).

Accordingly, it is possible to prevent accidents that may be caused due to drunk driving in advance. Further, since it is possible to prevent accidents that may be caused due to drunk driving in advance, if the driver D works for a company, it is possible to eliminate the risk of damaging the company's image.

Further, according to the second example embodiment, if it is determined that the movement direction ED of the driver D of the own vehicle V has been changed (Step S18: YES), the processing including prediction of the movement target position coordinates P2 of the driver D of the own vehicle V (Step S16) and setting of the estimated walking path C (Step S17) are repeatedly executed. That is, every time the movement direction ED of the driver D of the own vehicle V changes, a new estimated walking path C is set.

Accordingly, even if it is determined that the movement direction ED of the driver D of the own vehicle V has been changed, it is possible to continuously determine whether or not the driver D of the own vehicle V is drunk based on the walking pattern of the driver D of the own vehicle V.

Next, a modified example will be described.

While the example in which the drinking determination unit 13k determines whether or not the driver D of the own vehicle V has the walking pattern (see FIG. 6) in which he/she repeatedly keeps within and then goes outside of the width W2 of the estimated walking path C more than a predetermined number of times within a certain period of time, it is determined that the driver D of the own vehicle V is drunk if the walking pattern has been repeated more than the predetermined number of times, and it is determined that the driver D of the own vehicle V is not drunk if the above walking pattern has not been repeated more than the predetermined number of times has been described in the second example embodiment, this is merely an example.

That is, the drinking determination unit 13k may be a desired one as long as it determines whether or not the driver D of the own vehicle V is drunk based on the walking pattern of the driver D of the own vehicle V in the estimated walking path C. The drinking determination unit 13k determines, for example, whether or not the driver D of the own vehicle V (the current position coordinates of the driver D of the own vehicle V) has a walking pattern of moving away from the estimated walking path C and approaching to the estimated walking path C more than a predetermined number of times within a certain period of time. If the driver D has the above walking pattern, the drinking determination unit 13k may determine that the driver D of the own vehicle V is drunk. On the other hand, if the driver D has not repeated the above walking pattern, the drinking determination unit 13k may determine that the driver D of the own vehicle V is not drunk.

While the example of using a straight line that connects the current position coordinates P1 of the driver D of the own vehicle V and the movement target position coordinates P2 as the estimated walking path C has been described in the above second example embodiment, this is merely an example. For example, a curve that connects the current position coordinates P1 of the driver D of the own vehicle V and the movement target position coordinates P2 (for example, a curve that bypasses an obstacle between the driver D of the own vehicle V and the own vehicle V) may be used as the estimated walking path C.

Further, while the example of using the shoulder width W1 of the driver D of the own vehicle V detected by the shoulder width detection unit 13c as the width W2 of the estimated walking path C has been described in the above second example embodiment, this is merely an example. The width W2 of the estimated walking path C may be, for example, a numerical value (fixed value) stored in the storage unit 12 in advance.

The order that Steps S10-S20 are performed in the above second example embodiment is not limited to the order described above. For example, Steps S13, S14, and S15 may be performed in the order of Step S14, Step S13, and Step S15 or may be performed in another order.

In the above first and second example embodiments, the program(s) can be stored and provided to a computer using any type of non-transitory computer readable media. Non-transitory computer readable media include any type of tangible storage media. Examples of non-transitory computer readable media include magnetic storage media (such as flexible disks, magnetic tapes, hard disk drives, etc.), optical magnetic storage media (e.g., magneto-optical disks), CD-Read Only Memory (ROM), CD-R, CD-R/W, semiconductor memories (such as mask ROM, Programmable ROM (PROM), Erasable PROM (EPROM), flash ROM, Random Access Memory (RAM), etc.). Further, the program(s) may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

Needless to say, all the numerical values described in the above example embodiments are merely examples and numerical values other than those described above may be naturally used.

The above example embodiments are merely illustrative in all respects. The present invention should not be interpreted as being limited to the descriptions in the above example embodiments. The present invention may be implemented in other various forms without departing from the spirit and the main features of the present invention.

The whole or part of the example embodiments disclosed above can be described as, but not limited to, the following supplementary notes.

(Supplementary Note 1)

An in-vehicle apparatus comprising:
estimated walking path acquisition means for acquiring an estimated walking path, which is a path in which it is estimated that a driver will walk; and
drinking determination means for determining whether or not the driver is drunk based on a walking pattern of the driver with respect to the estimated walking path.

(Supplementary Note 2)

The in-vehicle apparatus according to Supplementary Note 1, further comprising:
current position coordinate detection means for detecting current position coordinates of the driver;
movement target position coordinate prediction means for predicting movement target position coordinates of the driver; and
estimated walking path setting means for setting the estimated walking path that connects the current position coordinates of the driver detected by the current position coordinate detection means and the movement target position coordinates of the driver predicted by the movement target position coordinate prediction means,
wherein the estimated walking path acquisition means acquires the estimated walking path set by the estimated walking path setting means.

(Supplementary Note 3)

The in-vehicle apparatus according to Supplementary Note 2, further comprising movement direction prediction means for predicting a movement direction of the driver,
wherein the movement target position coordinate prediction means predicts a position located away from the current position coordinates of the driver in the movement direction that has been predicted by the movement direction prediction means as the movement target position coordinates of the driver.

(Supplementary Note 4)

The in-vehicle apparatus according to Supplementary Note 3, wherein the movement direction prediction means predicts at least one of the line-of-sight of the driver and the orientation of the body of the driver as the movement direction of the driver.

(Supplementary Note 5)

The in-vehicle apparatus according to Supplementary Note 3 or 4, further comprising movement direction change determination means for determining whether or not the movement direction of the driver has been changed,
wherein, if it is determined by the movement direction change determination means that the movement direction of the driver has been changed, the movement target position coordinate prediction means predicts the movement target position coordinates of the driver.

(Supplementary Note 6)

The in-vehicle apparatus according to any one of Supplementary Notes 1 to 5, wherein the drinking determination means determines that the driver is drunk if the driver has a walking pattern in which he/she repeatedly keeps within and then goes outside of the width of the estimated walking path more than a predetermined number of times within a certain period of time.

(Supplementary Note 7)

The in-vehicle apparatus according to Supplementary Note 6, further comprising shoulder width detection means for detecting a shoulder width of the driver,
wherein the width of the estimated walking path is the shoulder width of the driver detected by the shoulder width detection means.

(Supplementary Note 8)

The in-vehicle apparatus according to any one of Supplementary Notes 1 to 5, wherein the drinking determination means determines that the driver is drunk if the driver has a walking pattern of moving away from the estimated walking path and approaching to the estimated walking path more than a predetermined number of times within a certain period of time.

(Supplementary Note 9)

The in-vehicle apparatus according to any one of Supplementary Notes 1 to 8, further comprising vehicle control means for controlling a vehicle that the driver is planning to drive if it has been determined by the drinking determination means that the driver is drunk.

(Supplementary Note 10)

The in-vehicle apparatus according to Supplementary Note 9, wherein, if it has been determined by the drinking determination means that the driver is drunk, the vehicle control means controls the vehicle in such a way that the engine of the vehicle that the driver is planning to drive cannot be started.

(Supplementary Note 11)

The in-vehicle apparatus according to Supplementary Note 9, wherein, if it has been determined by the drinking determination means that the driver is drunk, the vehicle control means locks the door of the vehicle that the driver is planning to drive so that the driver cannot open the door.

(Supplementary Note 12)

A drinking determination method comprising:
an estimated walking path acquisition step for acquiring an estimated walking path, which is a path in which it is estimated that a driver will walk; and
a drinking determination step for determining whether or not the driver is drunk based on a walking pattern of the driver with respect to the estimated walking path.

(Supplementary Note 13)

A computer readable storage medium that stores a program for causing an electronic device including at least one processor to execute the following processing of:
estimated walking path acquisition processing for acquiring an estimated walking path, which is a path in which it is estimated that a driver will walk; and
drinking determination processing for determining whether or not the driver is drunk based on a walking pattern of the driver with respect to the estimated walking path.

REFERENCE SIGNS LIST

1 In-vehicle Apparatus
11 Image-capturing Unit
12 Storage Unit
12a Program
12b Driver Information
13 Control Unit
13a Driver Recognition Unit
13b Current Location Coordinate Detection Unit
13c Shoulder Width Detection Unit
13d Visual Line and the like Detection Unit
13e Movement Direction Prediction Unit
13f Movement Target Location Coordinates Prediction Unit
13g Estimated Walking Path Setting Unit
13h Estimated Walking Path Acquisition Unit
13j Movement Direction Change Determination Unit
13k Drinking Determination Unit
13m Vehicle Control Unit
21 Estimated Walking Path Acquisition Means
22 Drinking Determination Means
C Estimated Walking Path
D Driver
ED Movement Direction
P1 Current Location Coordinates
P2 Movement Target Location Coordinates
V Own Vehicle
W1 Shoulder Width

The invention claimed is:

1. An in-vehicle apparatus comprising:
an image-capturing device,
at least one memory storing instructions, and
at least one processor configured to execute the instructions to:
detect current position coordinates of a driver;
detect a shoulder width of the driver;
detect at least one of a line-of-sight of the driver and an orientation of the body of the driver as a movement direction of the driver based on an image captured by the image-capturing device;
set an estimated walking path, which is a path in which it is estimated that the driver will walk from the detected current position coordinates;
set a width of the estimated walking path based on the detected shoulder width; and
determine whether or not the driver is drunk based on a walking pattern of the driver with respect to the estimated walking path with the set width, wherein determining whether or not the driver is drunk further comprises:
determining whether or not the movement direction of the driver has changed by more than a pre-determined threshold.

2. The in-vehicle apparatus according to claim 1, wherein:
the at least one processor is further configured to execute the instructions to
predict movement target position coordinates of the driver; and
set the estimated walking path that connects the detected current position coordinates of the driver and the predicted movement target position coordinates of the driver,
wherein the at least one processor is further configured to execute the instructions to acquire the set estimated walking path.

3. The in-vehicle apparatus according to claim 2, wherein the at least one processor is further configured to execute the instructions to predict the movement direction of the driver,
the at least one processor is further configured to execute the instructions to predict a position located away from the current position coordinates of the driver in the movement direction that has been predicted as the movement target position coordinates of the driver.

4. The in-vehicle apparatus according to claim 3, wherein the at least one processor is further configured to execute the instructions to determine whether or not the movement direction of the driver has been changed,
wherein, if it is determined that the movement direction of the driver has been changed, the at least one processor is further configured to execute the instructions to predict the movement target position coordinates of the driver.

5. The in-vehicle apparatus according to claim 1, wherein the at least one processor is further configured to execute the instructions to determine that the driver is drunk if the driver has a walking pattern in which he/she repeatedly keeps within and then goes outside of the width of the estimated walking path more than a predetermined number of times within a certain period of time.

6. The in-vehicle apparatus according to claim 1, wherein the at least one processor is further configured to execute the instructions to determine that the driver is drunk if the driver has a walking pattern of moving away from the estimated walking path and approaching to the estimated walking path more than a predetermined number of times within a certain period of time.

7. The in-vehicle apparatus according to claim 1, wherein the at least one processor is further configured to execute the instructions to control a vehicle that the driver is planning to drive if it has been determined that the driver is drunk.

8. The in-vehicle apparatus according to claim 7, wherein, if it has been determined that the driver is drunk, the at least one processor is further configured to execute the instructions to control the vehicle in such a way that the engine of the vehicle that the driver is planning to drive cannot be started.

9. The in-vehicle apparatus according to claim 7, wherein, if it has been determined that the driver is drunk, the at least one processor is further configured to execute the instructions to lock the door of the vehicle that the driver is planning to drive so that the driver cannot open the door.

10. A drinking determination method comprising:
   detecting current position coordinates of a driver;
   detecting a shoulder width of the driver;
   detecting at least one of a line-of-sight of the driver and an orientation of the body of the driver as a movement direction of the driver based on an image captured by the image-capturing device;
   setting an estimated walking path, which is a path in which it is estimated that the driver will walk from the detected current position coordinates;
   setting a width of the estimated walking path based on the detected shoulder width; and
   determining whether or not the driver is drunk based on a walking pattern of the driver in the estimated walking path with the set width, wherein determining whether or not the driver is drunk further comprises:
   determining whether or not the movement direction of the driver has changed by more than a pre-determined threshold.

11. A non-transitory computer readable storage medium that stores a program for causing an electronic device including at least one processor to execute the following processing of:
   detecting current position coordinates of a driver;
   detecting a shoulder width of the driver;
   detecting at least one of a line-of-sight of the driver and an orientation of the body of the driver as a movement direction of the driver based on an image captured by the image-capturing device;
   setting an estimated walking path, which is a path in which it is estimated that the driver will walk from the detected current position coordinates;
   setting a width of the estimated walking path based on the detected shoulder width; and
   determining whether or not the driver is drunk based on a walking pattern of the driver in the estimated walking path with the set width, wherein determining whether or not the driver is drunk further comprises:
   determining whether or not the movement direction of the driver has changed by more than a pre-determined threshold.

* * * * *